United States Patent
Mahoney et al.

(10) Patent No.: US 8,803,643 B2
(45) Date of Patent: Aug. 12, 2014

(54) CONTROL OF MAGNETICALLY ACTUATED TOOLS IN ANY POSITION USING A ROTATING MAGNETIC SOURCE

(75) Inventors: Arthur W. Mahoney, Salt Lake City, UT (US); Jacob J. Abbott, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 81 days.

(21) Appl. No.: 13/330,300

(22) Filed: Dec. 19, 2011

(65) Prior Publication Data

US 2013/0154776 A1    Jun. 20, 2013

(51) Int. Cl.
 H01F 7/00 (2006.01)
 H01F 7/02 (2006.01)
 A61B 1/00 (2006.01)
 A61B 1/04 (2006.01)

(52) U.S. Cl.
 CPC .. H01F 7/00 (2013.01); H01F 7/02 (2013.01); A61B 1/00158 (2013.01); A61B 1/041 (2013.01)
 USPC ............................. 335/219; 600/101; 600/117

(58) Field of Classification Search
 CPC ........... H01F 7/00; H01F 7/02; H01F 7/0247; A61B 1/041; A61B 1/00158; A61B 2019/2253; A61B 19/22; A61B 19/2203
 USPC ................... 335/200, 216; 600/101, 117, 118
 See application file for complete search history.

(56) References Cited

U.S. PATENT DOCUMENTS

| | | | |
|---|---|---|---|
| 7,962,194 B2 * | 6/2011 | Martel et al. | 600/411 |
| 2007/0244388 A1 * | 10/2007 | Sato et al. | 600/424 |
| 2010/0264776 A1 * | 10/2010 | Vollmers et al. | 310/300 |
| 2011/0184235 A1 * | 7/2011 | Schostek et al. | 600/109 |
| 2012/0101333 A1 * | 4/2012 | Takahashi et al. | 600/118 |
| 2012/0168233 A1 * | 7/2012 | Clark | 180/8.1 |

* cited by examiner

*Primary Examiner* — Bernard Rojas
(74) *Attorney, Agent, or Firm* — Thorpe North & Western LLP (57) ABSTRACT

Systems and methods utilize a rotating magnetic field to drive a magnetically actuated device where the source of the rotating magnetic field is not constrained to a particular orientation with respect to the device. In one embodiment a rotating permanent magnet is utilized to actuate a magnetically actuated device where the magnet is not constrained to any position relative to the magnetically actuated device, such as the radial or axial position. Accordingly, the rotating permanent magnet may be directed in a manner to avoid collisions or other obstacles in a workspace while still effectively driving the magnetically actuated device.

19 Claims, 10 Drawing Sheets

CONTROL OF MAGNETICALLY ACTUATED TOOLS IN ANY POSITION USING A ROTATING MAGNETIC SOURCE

This invention was made with government support under Grant or Award nos. IIS-0952718 and DGE-0654414 awarded by The National Science Foundation. The government has certain rights in this invention

TECHNICAL FIELD

The present application is directed toward image guiding magnetically actuated devices.

BACKGROUND OF THE INVENTION

Untethered magnetic devices, such as magnetic microrobots and magnetically actuated capsule endoscopes, have become an active area of research because of their potential impact to minimally invasive medicine. These devices typically consist of a rigidly attached magnetic body on which magnetic forces and torques are applied by an external field. Some approaches to actuation utilize magnetic forces for pulling, while others apply torque generated by rotating magnetic fields to roll on a surface, swim through a fluid or crawl through a lumen via helical propulsion, or screw through soft tissue. Because these devices can be viewed as simple end-effectors of a larger robotic system, and they may range in size from the microscale to the mesoscale, such devices are referred to herein as magnetically actuated tools (MATs) without any implied size.

Currently, MATs are typically actuated using applied magnetic fields produced by electromagnets, often taking the form of orthogonal arrangements of Helmholtz or Maxwell coils. Such coils are generally small and work in a laboratory setting. However, scaling electromagnetic coils to sizes suitable to create fields for use with MATs inside a human body is currently difficult.

Because electromagnetic coil systems are expensive to scale to the size required for clinical use, researchers are considering actuation using a single permanent magnet outside of a patient's body. Although less expensive, actuation with permanent magnets is significantly more complex because applied magnetic force and torque cannot be controlled independently (although some force management strategies exist). In the case of MAT locomotion using rotating applied fields generated by a single rotating permanent magnet (RPM), the RPM is typically rotated around an axis $\hat{\Omega}$ such that the RPM's dipole moment M is always perpendicular to $\hat{\Omega}$ as depicted in FIG. 1.

Figure 1A:
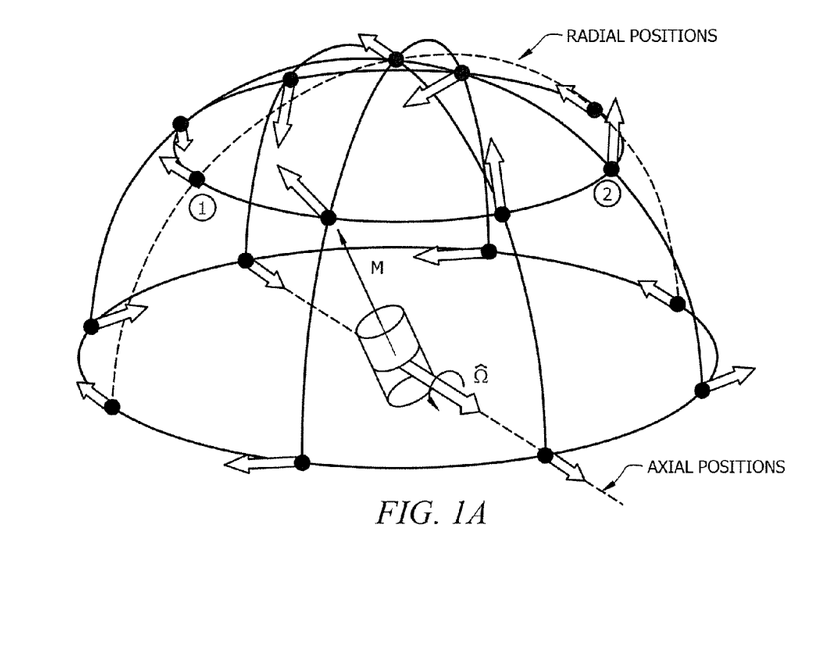
FIGS. 1a and 1b illustrate the rotation axis of applied magnetic fields caused by a rotating magnetic-dipole field source.
Figure 1B:
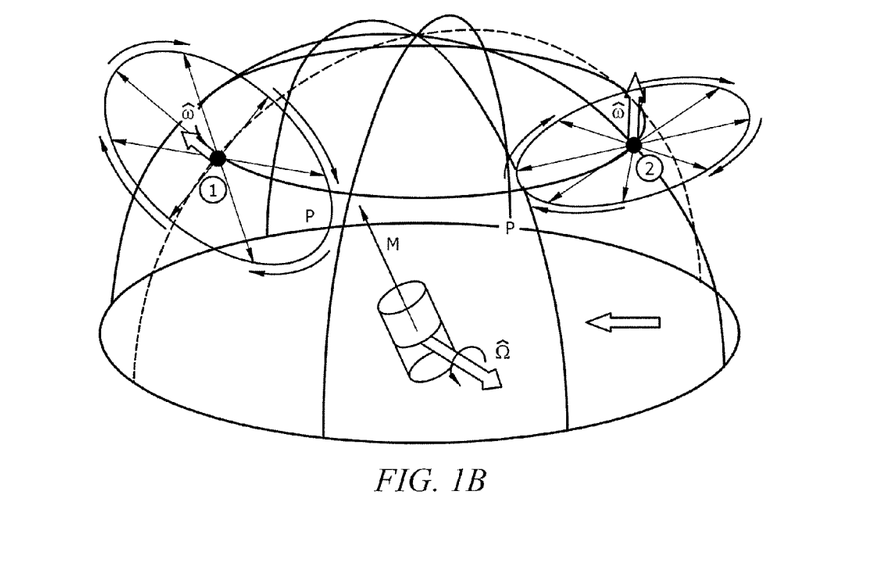

As shown in FIGS. 1a-1b, when a dipole magnet with moment M rotates around the axis $\hat{\Omega}$ with M perpendicular to $\hat{\Omega}$, the field vector at any given position rotates around, and is perpendicular to, a constant axis $\hat{\omega}$. The axis $\omega$ at various positions are illustrated with arrows in (a). Any position on the $\hat{\Omega}$ axis is denoted to be in an axial position and any position in the plane spanned by the rotating M is a radial position. Representations of the field behavior at locations 1 and 2 are detailed in (b).

To date, MATs have been exclusively operated in radial or axial positions (relative to the RPM) where the applied field rotates around an axis parallel to $\hat{\Omega}$ (see FIG. 1a). The axial and radial positions have been historically favored for actuation due to their simplicity: the rotation axis $\hat{\omega}$ of the applied magnetic field in both positions lies parallel to the RPM axis of rotation, making it easy to visualize and characterize the coupling between the RPM and the MAT.

Requiring the MAT to be exclusively operated in these two positions, however, significantly constrains the physical placement of the RPM. This is because the large permanent magnet needs to follow the MAT when navigating through the human body and must be precisely positioned in order to achieve correct motion of the device. These workspace limitations become problematic and limit usefulness of RPMs in a clinical setting since the RPM must move during actuation to avoid collisions with the patient and other obstacles, and reposition for better control authority.

SUMMARY

The present application provides for systems and methods that utilize a rotating magnetic field to drive a magnetically actuated device where the source of the rotating magnetic field is not constrained to a particular orientation with respect to the device. In one embodiment an RPM is utilized to actuate a MAT where the RPM is not constrained to any position relative to the MAT, such as the radial or axial position. Accordingly, the RPM may be directed in a manner to avoid collisions or other obstacles in a workspace while still effectively driving the MAT.

It has been shown that when a dipole (e.g., RPM) rotates such that its moment is always perpendicular to the axis of rotation, the generated field at any position in space rotates around, and is perpendicular to, a constant axis (FIG. 1a) with field magnitude described by an ellipse (FIG. 1b). Embodiments of the present application reformulate this phenomenon which enables the solution of the inverse problem: finding the necessary RPM rotation axis $\hat{\Omega}$ given a desired applied field rotation axis $\hat{\omega}$ for any RPM position relative to the MAT. As a result, a rotating magnetic field may be produced around an arbitrary axis $\hat{\omega}$ in space using a single RPM in any position and controlling MATs actuated by a single RPM becomes clinically realistic.

In accordance with one embodiment, an apparatus is presented that actuates a magnetically actuated device. The apparatus includes a rotating magnetic field source and a guiding device. The guiding device is configured to hold the rotating magnetic field source and to reposition the rotating magnetic field source in order to actuate the magnetically actuated device. Additionally, the repositioning of the rotating magnetic field source is not constrained to a particular position with respect to the magnetically actuated device.

Another embodiment provides a method for propelling a microrobot. The method includes the steps of providing a magnetic field generating source. The magnetic field generating source is rotated about an axis of rotation, thereby creating magnetic torques and forces at a separate point in space. Additionally, the magnetic field source is repositioned to propel the microrobot with the created magnetic torques and forces, wherein said repositioning follows an unconstrained trajectory with respect to the microrobot.

Yet another embodiment provides a method for driving a magnetically actuated device. The method includes locating the magnetically actuated device within a body of a patient. A rotating permanent magnet is then positioned proximate to said patient and rotated in order to provide magnetic torques and forces to said magnetically actuated device. The rotating permanent magnet is also repositioned in a manner to guide said magnetically actuated device through the patient's body, wherein this repositioning follows a free trajectory with respect to the magnetically actuated device, and also accounts for workspace limitations.

The foregoing has outlined rather broadly the features and technical advantages of the present invention in order that the detailed description of the invention that follows may be better understood. Additional features and advantages of the invention will be described hereinafter, which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION

While the following description discusses guiding untethered magnetic devices (such as MATs) in the context of guiding a device within a human body, it is noted that this discussion is provided by way of example in order to describe capabilities of embodiments of the present application. The concepts utilized to guide such devices may be utilized to guide these devices in various mediums which may be applicable, e.g. within other animals, within contained water environments, and the like.

Figure 2:
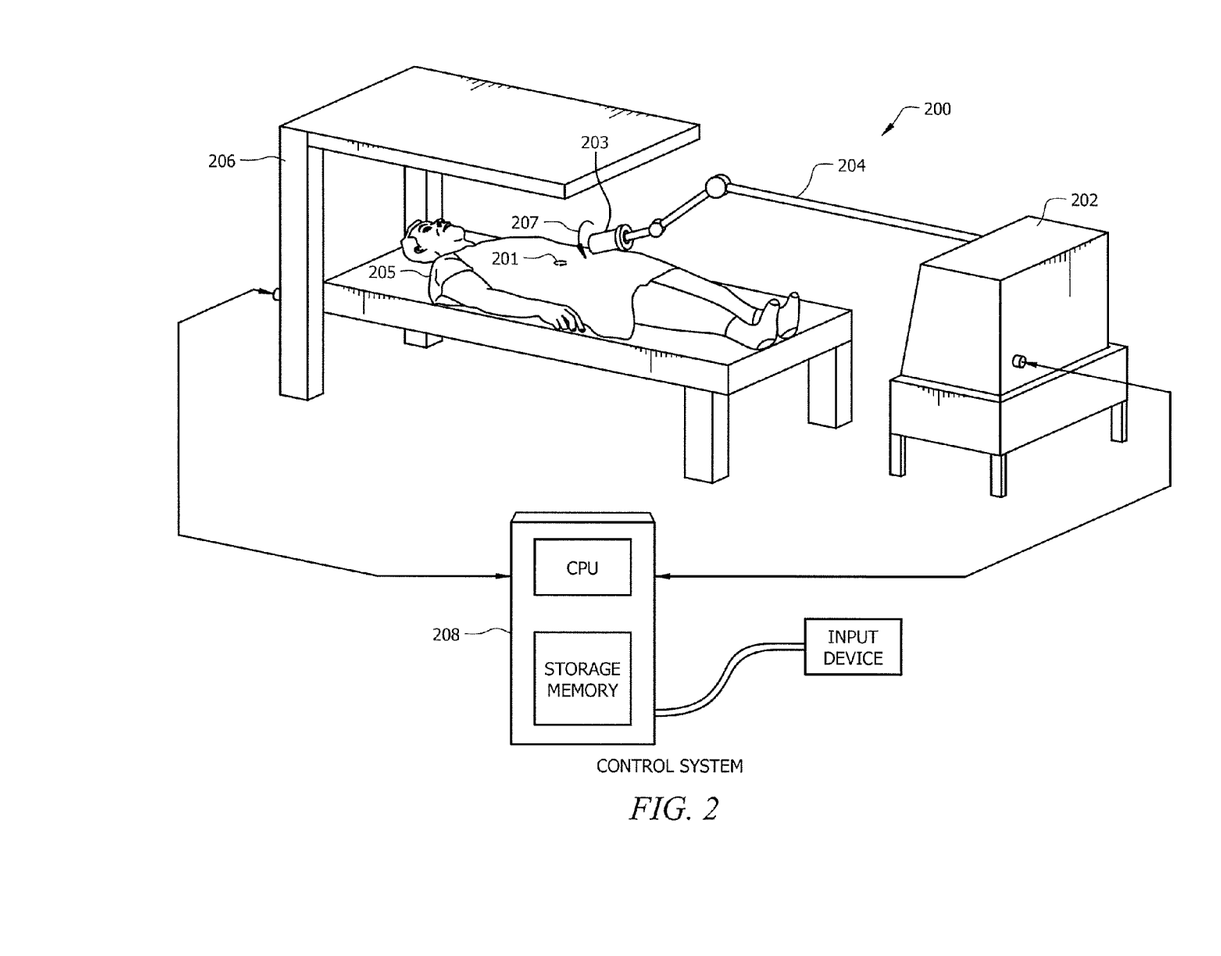
FIG. 2 illustrates a system for guiding a magnetically actuated device.

FIG. 2 illustrates a system 200 for guiding a magnetically actuated device, such as MAT 101 using a rotating magnetic field provided by rotating magnetic field apparatus 202. Rotating magnetic field apparatus 202 includes a rotating magnetic field source 203, which in the illustrated embodiment is an RPM. In some embodiments, rotating magnetic field apparatus includes a robotic arm 204 having six degrees of freedom of motion such that it may orient rotating magnetic field source 203 with respect to a subject, such as patient 205, without colliding with other obstacles in the workspace, such as imaging system 206. Rotating magnetic field apparatus 202 may also provide the driving torque to rotate an RPM in a direction about a rotation axis 207.

Imaging system 206 may include any type of imaging system which will not inhibit the magnetic properties and desired functionality of MAT 201 and rotating magnetic field source 203. For example, imaging system 206 may include an x-ray machine, CT scanning machine, fluoroscopy machine, ultrasound device, and the like. Imaging system 206 is generally used to monitor the position of MAT 201 (either continuously, or periodically) to assist with proper orientation of rotating magnetic field apparatus 202 and rotating magnetic field source 203 such that these devices may be oriented in a manner which allows for providing effective actuation forces to MAT 201.

System 200 further includes control system 208. Control system 208 includes a central processing unit 209, storage/memory 210 and an input configured to receive instructions from a user via input device 211. Control system 208 may be configured to send and receive control signals between one or more of imaging system 206 and rotating magnetic field apparatus 202.

Control system 208 may include software having instruction sets which enable magnetic field apparatus 202 to position magnetic field source 203 in a manner to direct MAT 201. Control system 208 may also control magnetic field apparatus 202 in a manner to avoid collisions with workspace obstacles such as patient 205, imaging system 206, and the like. Such direction may be implemented automatically and/or with the assistance of a user providing information via input device 211.

In some embodiments, control system 208 may utilize information received from imaging system 206 to locate MAT 201. With such information, control system 208 may then direct magnetic field apparatus 202 and position magnetic field source 203 in a manner to direct MAT 201. Further, in some embodiments a separate control systems may be utilized for imaging system 206 and magnetic field apparatus 202. These separate systems may function independently, or may be in communication with each other to provide controls to portions of system 200.

Figure 3:
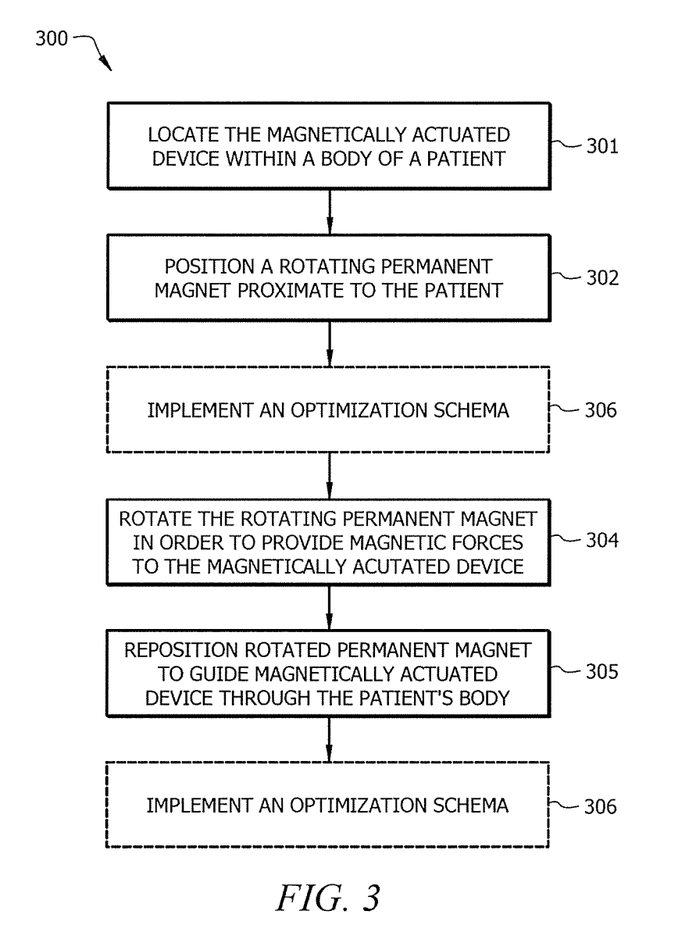
FIG. 3 illustrates a flowchart corresponding to a method for driving a magnetically actuated device.

FIG. 3 illustrates a flowchart corresponding to a method 300 for driving a magnetically actuated device. The method includes locating the magnetically actuated device within a body of a patient 301. In some embodiments, such location may be implemented using an imaging system, such as imaging system 206. Alternatively, embodiments may locate the magnetically actuated device using means included within the device itself, such as an RFID, magnetic field measurements from fields caused by the device, signals received from the device (e.g. video signals from a magnetically actuated device acting as a scope, feedback information from sensors on the device containing information regarding the source field), and the like.

It is further noted that in some embodiments, the location of an MAT may be visibly seen (e.g. generally in non medical applications) and such a visual location may be used to calibrate the positioning of the magnetic field source. Moreover, in some embodiments a locating step may be bypassed and knowledge about probable location may be utilized to calibrate the positioning of the magnetic field source.

With the position of the magnetically actuated device known, method 300 positions a rotating permanent magnet proximate to the patient at step 302. Such positioning is implemented in light of where the rotating permanent magnet is able to create magnetic torques to act on the MAT. However, embodiments may or may not require that the position have a specific orientation with respect to the MAT.

With the rotating permanent magnet in position, the method rotates the rotating permanent magnet in order to provide magnetic torques to the magnetically actuated device at step 303. Such rotation generates friction to propel the MAT. Additionally, the rotating permanent magnet is repositioned in a manner to guide said magnetically actuated device through the patient's body at step 304. This repositioning follows a free trajectory with respect to the magnetically actuated device, but also accounts for workspace limitations. For example, the motion of the rotating field source position and subsequent repositioning is not constrained to be in the axial or radial positions with respect to the MAT. Additionally, such motion may take into account various workspace constraints to prevent collisions with a patient, imaging systems, and the like.

It is noted that the above method steps are provided by way of example and various steps may implemented in a different order, multiple times, and/or even omitted. Further, additional steps may be included. For example, when positioning/repositioning a permanent magnet in step 302 or 304, embodiments may implement an optimization schema (step 305) which takes into account the strength of magnetic forces which are possible in a new position as well as other factors. It may be that a second or third most optimal position may be selected in light of other factors, such as potential workspace obstructions.

While the present application has discussed a MAT in general terms, it is noted that such MAT's may have various applications, e.g. capsule endoscopes, tools for drug delivery, magnetic screws capable of being driven through soft tissue, biopsy tools, and the like. Such a device could be swallowed by the patient and then driven through their GI tract. Moreover, such a device could be used to replace a traditional colonoscopy, e.g. inserted rectally and then driven around in the large and small intestine. The present application is not limited to the type of device being actuated.

The following discussion provides example methods for controlling local field rotation, controlling rotating magnetically actuated tools, and example results in accordance with embodiments of the present application. It is noted that the following is presented by way of example and that various modifications may be made based on the types of equipment being utilized, particular applications, and the like. Such modifications are considered within the scope of the novel concepts described in the present application.

Controlling Local Field Rotation

Vectors described in this application are expressed in a common, static coordinate frame, and the "hat" symbol denotes a vector normalized to unit length. Let the RPM's dipole moment M rotate around the axis $\hat{\Omega}$ such that M is always perpendicular to $\hat{\Omega}$, and the direction of rotation is found using a right-hand rule. Assuming the magnetic field generated by the RPM can be accurately modeled with the point-dipole model, the magnetic field H at a position p relative to the center of the RPM is $$H = \frac{1}{4\pi|p|^3}(3\hat{p}\hat{p}^T - \mathbb{I})M = \frac{1}{4\pi|p|^3}\mathbb{H}M \qquad (1)$$

where I is the identity matrix and $\hat{p}$ is the unit vector in the direction of p. The matrix H is symmetric and is purely a function of $\hat{p}$. Let the vector $\hat{\omega}$ be the desired rotation axis of the local magnetic field at the position p, where $\hat{\omega}$ is normal to the plane containing H, such that $H^T\hat{\omega}=0$ for all M. Replacing H with (1) in this expression and utilizing the symmetry of H yields $$H^T\hat{\omega}=M^TH\hat{\omega}=0 \qquad (2)$$

Because $H\hat{\omega}$ is constant and $M^T\hat{\Omega}=0$, the solution for the necessary dipole axis of rotation $\hat{\Omega}$ where $\hat{\Omega}$ is parallel to $H\hat{\omega}$ is the only solution invariant to the rotation of M. Therefore, given $\hat{\omega}$ and $\hat{p}$, $\hat{\Omega}$ can be found with $$\hat{\Omega}=\widehat{H\hat{\omega}} \qquad (3)$$

Because H is constructed using the unit vector $\hat{p}$, H changes with changes in the direction of $\hat{p}$. This implies that solutions obtained from (3) are invariant to scaling |p| by moving the RPM nearer to or farther away from the MAT, provided that the direction of p remains unchanged. Naturally, the magnitude of the field will depend on |p|. It can be verified using (1) that the eigenvectors of H include $\hat{p}$ and a 2-dimensional eigenspace consisting of vectors in the plane orthogonal to $\hat{p}$, with corresponding eigenvalues $\lambda_1=2$ and $\lambda_{2,3}=-1$, respectively. Because $\det(H)=\lambda_1\lambda_2\lambda_3=2$ for all p, H is always invertible and there exists exactly one dipole rotation axis $\hat{\Omega}$ to generate a desired field rotation about the axis $\hat{\omega}$ for any MAT position p. The forward problem, which gives the local field axis of rotation $\hat{\omega}$ at the position p given the RPM axis of rotation $\hat{\Omega}$, is found with $$\hat{\omega}=\widehat{H^{-1}\hat{\Omega}} \qquad (4)$$

An explicit representation of can be found using $$H^2=H+2I \qquad (5)$$

derived using the definition of H in (1) and recognizing that $\hat{p}^T\hat{p}=1$. Multiplying both sides of (5) by $H^{-1}$ produces the relation $H=I+2H^{-1}$ and subsequently $$H^{-1}=\frac{1}{2}(H-I) \qquad (6)$$

requiring no matrix conversion.

In practice, the position p of the MAT relative to the RPM can be measured using a variety of methods such as computer vision, medical imaging, or magnetic localization. With p and the desired applied field rotation axis $\hat{\omega}$ known, the necessary actuator axis of rotation $\hat{\Omega}$ can be quickly found by (3). As the MAT or the RPM moves and the direction of p changes, (3) must be updated by repacking the matrix H, and a new solution $\hat{\Omega}$ must be produced to maintain the desired applied field rotation axis at p. Although the process of solving (3) for $\hat{\Omega}$ can be theoretically performed independently from RPM path planning, in practice, the path and $\hat{\Omega}$ will be chosen to avoid hardware collisions while maintaining control authority over the MAT.

Controlling Rotating Magnetically Actuated Tools

For rotating MATs such as helical microswimmers, active capsule endoscopes, or those whose form of locomotion employs rolling, there exists a rotating field frequency above which the applied magnetic torque is too weak in magnitude to keep the MAT synchronized with the rotating field. This frequency is referred to as the "step-out" frequency and is denoted by $|\omega|_{max}$. For MATs whose rotational dynamics are dominated by the effects of linear damping proportional to angular speed (e.g., viscous drag) and inertia is negligible, the step-out frequency depends on the linear damping coefficient c and the magnitude of the applied magnetic torque. The linear damping torque is typically modeled with $\tau_d=c|\omega|$, where $|\omega|$ is the magnitude of the MAT's angular velocity, and the magnetic torque is given by $\tau_m=\mu_0 m \times H$ with magnitude $|\tau_m|=\mu_0|m||H|\sin(\alpha)$ where $\mu_0$ is the permeability of free space, m is the dipole moment of the magnetic body attached to the MAT, and $\alpha$ is the lead angle between the rotating applied field H and m. The step-out frequency occurs when $\alpha=90$ and is given by $|\omega|=\mu_0|m||H|/c$.

As the RPM rotates about $\hat{\Omega}$ and the local field at p rotates about $\hat{\omega}$, the magnitude of the field $|H|$ fluctuates in an elliptical fashion, making the step-out frequency of a MAT non-constant through each actuator revolution. The instantaneous field magnitude is $$|H| = \frac{|M|}{4\pi|p|^3}\sqrt{1+3(\hat{M}^T\hat{p})^2} \quad (7)$$

and the minimum and maximum field magnitudes are $$|H|_{min} = \frac{|M|}{4\pi|p|^3} \quad (8)$$

$$|H|_{max} = \frac{|M|}{4\pi|p|^3}\sqrt{1+3|\tilde{p}|^2} \quad (9)$$

where the vector $$\tilde{p}=(I-\hat{\Omega}\hat{\Omega}^T)\hat{p} \quad (10)$$

is the projection of $\hat{p}$ onto the plane perpendicular to $\hat{\Omega}$ (the plane in which M resides). The maximum field magnitude occurs when M is parallel to $\tilde{p}$ and the minimum field magnitude occurs when M is perpendicular to $\tilde{p}$. In the special case of $\hat{\omega}=\hat{p}$, corresponding to the axial positions depicted in FIG. 1a, then $\tilde{p}=0$ and $|H|_{min}=|H|_{max}$. With the field magnitude varying from $|H|_{min}$ to $|H|_{max}$, the step-out frequency consequently varies from $\mu_0|m||H|_{min}/c$ to $\mu_0|m||H|_{max}/c$ through each RPM revolution. Although the field magnitude cannot be controlled explicitly in this example, $|p|$ can be adjusted by moving the RPM close enough to the MAT, without changing the solution for $\hat{\omega}$, such that $|H|_{min}$, and thus the min minimum step-out frequency, are sufficient for the desired application. It is also theoretically possible to adjust $|p|$ dynamically throughout each RPM cycle such that $|H|$, and thus the step-out frequency, remains constant even when p is not in an axial position.

Aside from varying local field magnitude, the instantaneous angular velocity of the applied field as it rotates around $\hat{\omega}$ also varies through each cycle. If $\omega$ and $\Omega$ denote the instantaneous angular velocities of the local field and the RPM, respectively, then the relationship between $|\omega|$ and $|\Omega|$ can be found as $$|\omega| = \frac{\sqrt{1+3|\tilde{p}|^2}}{1+3(\hat{M}^T\hat{p})^2}|\Omega| \quad (11)$$

Comparing (11) to (7) shows that the maximum applied field angular velocity $|\omega|$, when $|\Omega|$ is constant, occurs at the instant when the magnetic field strength is the weakest. Because rotating the field faster than the step-out frequency causes the MAT to become unsynchronized with the field, the instantaneous RPM angular velocity $|\Omega|$ may be limited so that the field angular velocity $|\omega|$ given by (11) is always less than or equal to the step-out frequency $|\omega|_{max}$, which is time-varying itself.

Example Experimental Result

The RPM used in this example comprises a cylindrical 25:4 mm diameter, 25.4 mm long, Grade-N42, diametrically magnetized NdFeB permanent magnet driven by a Maxon 24V A-Max DC motor with an Advanced Motion Controls servo control drive and amplifier. The RPM is positioned with a Yaskawa Motoman MH5 6-DOF robotic manipulator.

Figure 4:
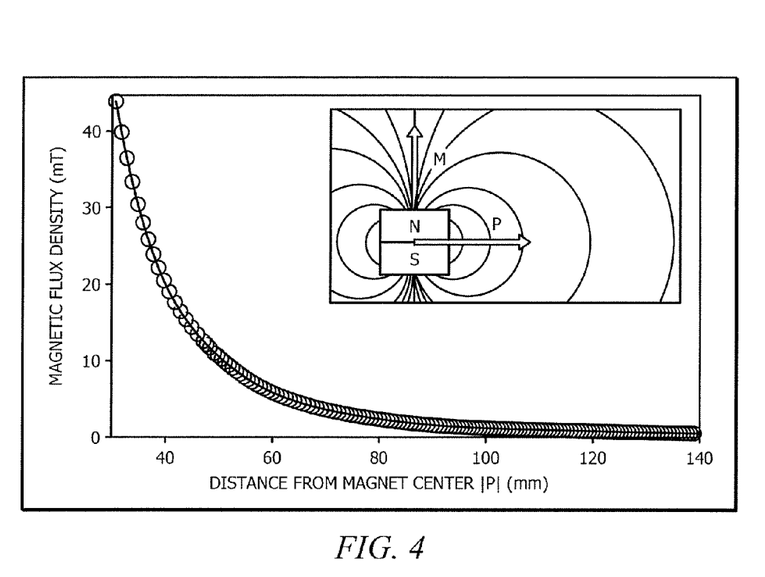
FIG. 4 is an exemplary graph illustrating the point-dipole model fit to a measured magnetic field.

The theory presented in the above discussion assumes that the magnetic field produced by the RPM can be modeled with the point-dipole model (1). The point-dipole model exactly predicts the field produced by a spherical permanent magnet and is an approximation for every other geometry that becomes accurate in the far field region. The magnetic field (magnetic flux density) of the RPM in this example is measured using a custom-made three-axis sensor. The sensor may be constructed using three pairs of Allegro A1301 linear Hall effect sensors mounted on the six sides of a 7 mm cube. In one example, each sensor has a sensitivity of 25 V/T and a range of ±0.1 T. The average measured value of the pair of sensors on two opposing faces approximates the component of the magnetic field at the cube's center in the normal direction to the faces. The dipole moment M of the RPM 501 (FIG. 5) was found using a least-squares fit of the point-dipole model to 100 samples of the field measured every millimeter between 30 mm and 140 mm from the RPM center, resulting in $|M|=12.7$ A·m$^2$ with $R^2=0.999$. The data and the fit are shown in FIG. 4.

Figure 5A:
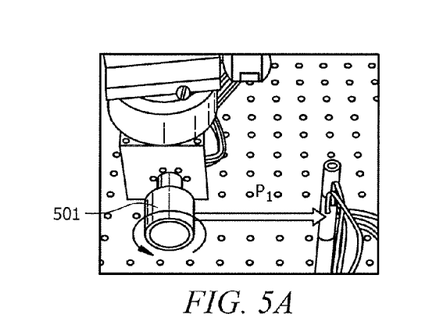
FIGS. 5a and 5b are exemplary illustrations of measurements of the magnetic field while rotating the RPM at two arbitrary positions.
Figure 5B:
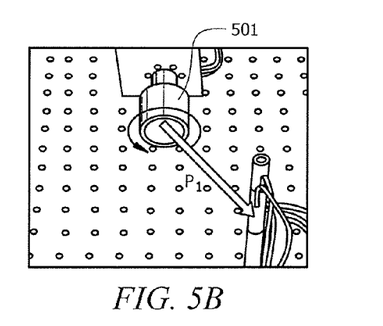
Figure 5C:
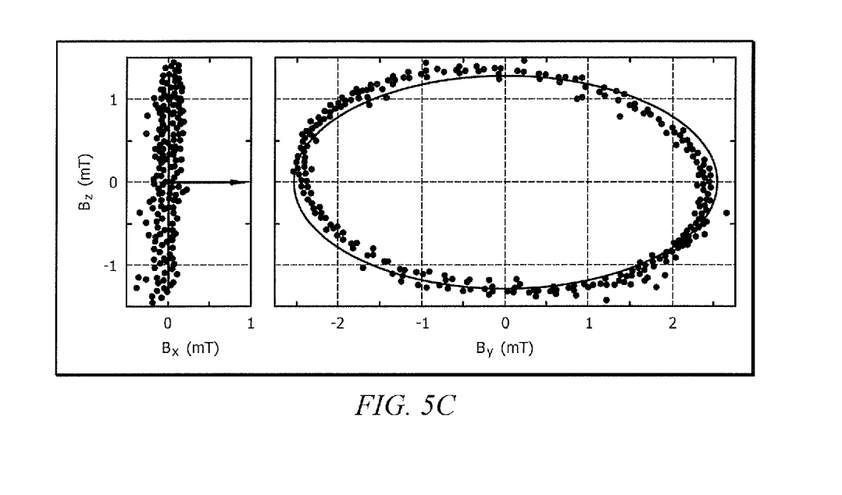
FIGS. 5c and 5d show the measured and predicted magnetic fields and axes of rotation at positions illustrated in FIGS. 5a and 5b projected into the x-z and y-z planes.
Figure 5D:
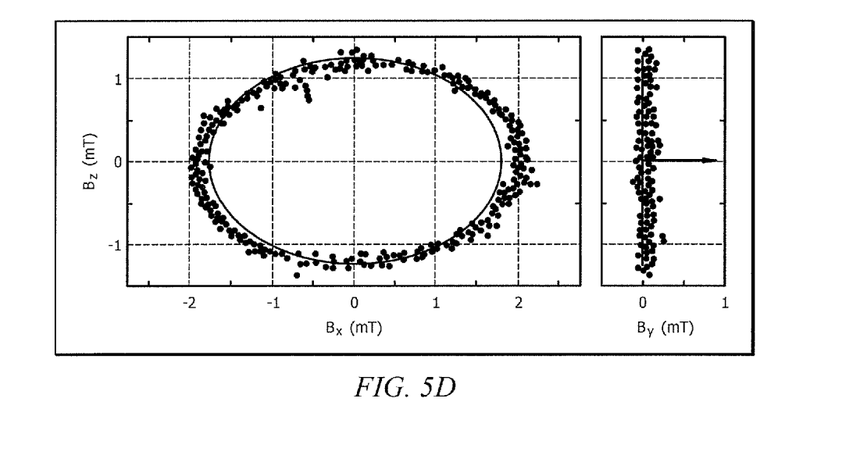

The accuracy of the fit and the correctness of the theory presented in the above discussion has been verified by measuring the magnetic field while rotating the RPM at two arbitrary positions located 100 mm from the RPM center. The positions $p_1=[0,100,1]^T$ mm shown in FIG. 5a and $p_2=[81.61, 57.79,0]^T$ mm shown in FIG. 5b are described in a stationary coordinate system with axes {x, y, z} such that $\hat{\Omega}$ corresponds to the x axis and the origin is located at the RPM center. FIGS. 5c and 5d show the measured and predicted magnetic fields and axes of rotation at both positions projected into the x-z and y-z planes. The RPM was rotated at a constant angular velocity of 1 rad/s in both positions. The predicted $\hat{\omega}$, obtained by (4), differed from the measured $\hat{\omega}$, obtained using principal component analysis (the direction of least variance), by 2.94° for $p_1$ and 0.73° for $p_2$. FIGS. 5a-5d show that the RPM magnetic field and its axis of rotation is closely predicted by the point-dipole model with $|M|=12.7$ A·m$^2$, even using an imperfect, custom-made magnetic-field sensor.

The control of rotating MATs by actuating a rolling spherical device and a threaded capsule-shaped device that produces forward motion along its principal axis from rotation around the same axis is demonstrated. Such motion may also be produced in a spiraling pattern. Both rotating MATs used in this example contain a 6.35 mm cubic Grade-N52 NdFeB magnet positioned near the device's center-of-gravity. The MATs were constrained during experimentation in a clear PVC lumen with 22.2 mm inner diameter, lightly lubricated with personal lubricant jelly. Applications where MATs are constrained in a lumen include capsule endoscopy and any medical procedure that could utilize a device which can maneuver through pathways in the urinary system, the subarachnoid space of the nervous system, or the cardiovascular system.

To date, rotating MATs have been actuated in axial or radial positions where the applied field rotation is easy to visualize and the coupling between the RPM and the MAT is easy to understand. In the radial position, for example, the magnetic field rotates around an axis parallel to that of the RPM, although in the opposite direction.

Figure 6A:
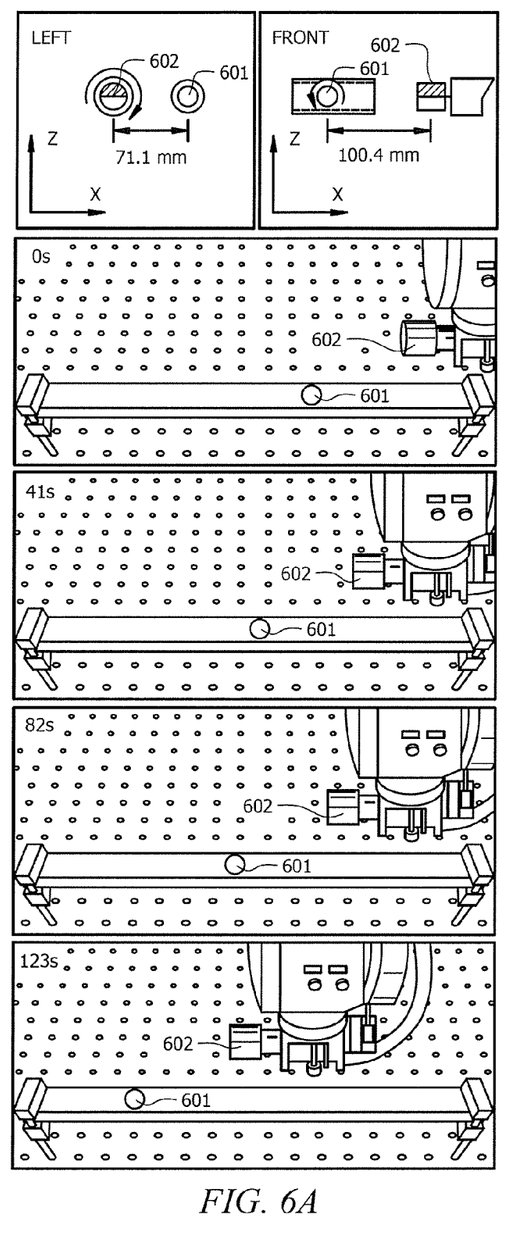
FIGS. 6a and 6b demonstrate two different MATs (rolling and threaded) being driven with $\hat{\Omega}$ perpendicular to the desired $\hat{\omega}$.
Figure 6B:
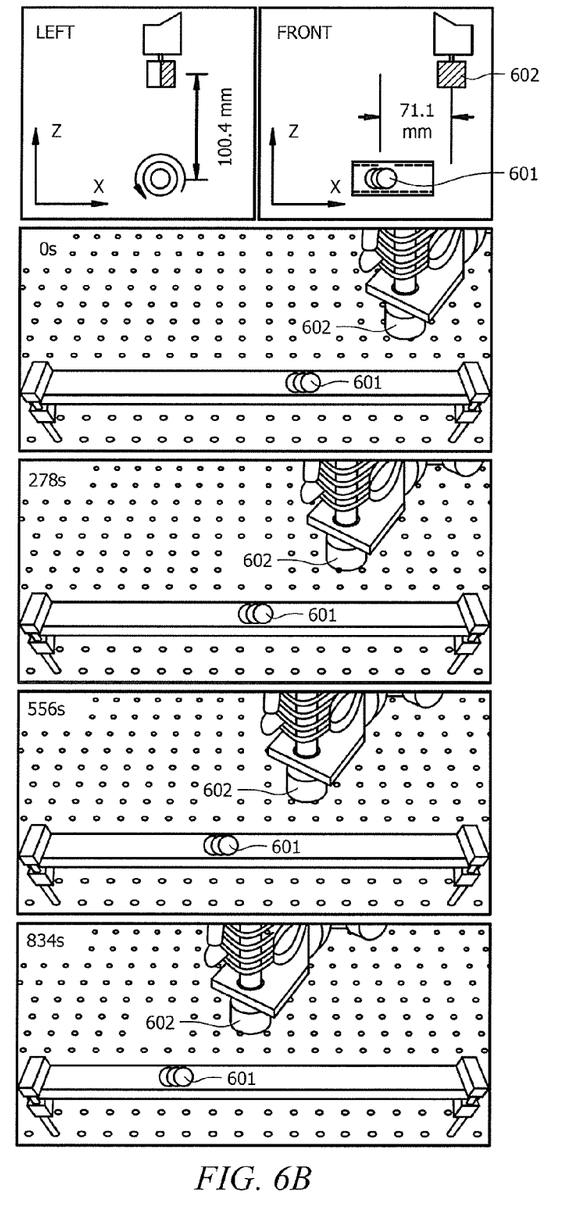

Applying the inventive concepts described herein enables operation of MATs in nonintuitive ways. FIG. 6 demonstrates two different MATs 601 (spherical/rolling and threaded/spiraling) being driven by an RPM 602 with $\hat{\Omega}$ perpendicular to the desired $\hat{\omega}$. This happens when the angle between $\hat{\Omega}$ and $\hat{p}$ is 35.3°. FIG. 6a shows the rolling MAT 601 actuated with $p=[71.1,-100.4,0]^T$ mm. With $\hat{\Omega}$ in the negative y direction in this position, (4) shows that $\hat{\omega}$ lies in the positive x direction and causes the spherical MAT 601 to roll down the lumen. The threaded capsule MAT is actuated with $p=[0,-71.1,-100.4]^T$ mm as shown in FIG. 6b. In this configuration, $\hat{\Omega}$ lies in the negative z direction to produce $\hat{\omega}$ parallel to the lumen. $|\Omega|=1.0$ rad/s and $|p|=123$ mm for both devices.

The configurations and speed used in the experiments of FIGS. 6a and 6b were chosen to clearly demonstrate the usefulness of the method proposed herein. Although the example could have been demonstrated with any $\hat{p}$ by applying (4), the configurations used in FIGS. 6a and 6b were selected because $\hat{\omega}$ is perpendicular to $\hat{\Omega}$ in both arrangements, which is particularly nonintuitive. In both configurations, the position of the RPM is effectively behind the MAT, such that the magnetic force that attracts the MAT toward the RPM opposes the primary propulsion method (e.g., rolling or helical propulsion). This was done to definitively demonstrate that the MAT is moving due to the rotating propulsion mechanism, which relies on the correct alignment of $\hat{\omega}$, rather than being pulled by magnetic forces. The speeds used are intentionally very slow, with an RPM angular velocity of only 1 rad/s. Slowly rotating the MAT tends to leave its dipole in an orientation relative to the applied field that maximizes the attractive force between the MAT and the RPM, making this demonstration a possible worst-case scenario. Because the RPM can control the rotating MAT from any position, in a clinical application, the position and angular velocity of the RPM may be optimized such that the magnetic force assists in propulsion, rather than hinders it. In some cases, the attractive magnetic force cannot be used for propulsion and must be managed or significantly reduced to prevent trauma.

Figure 7A:
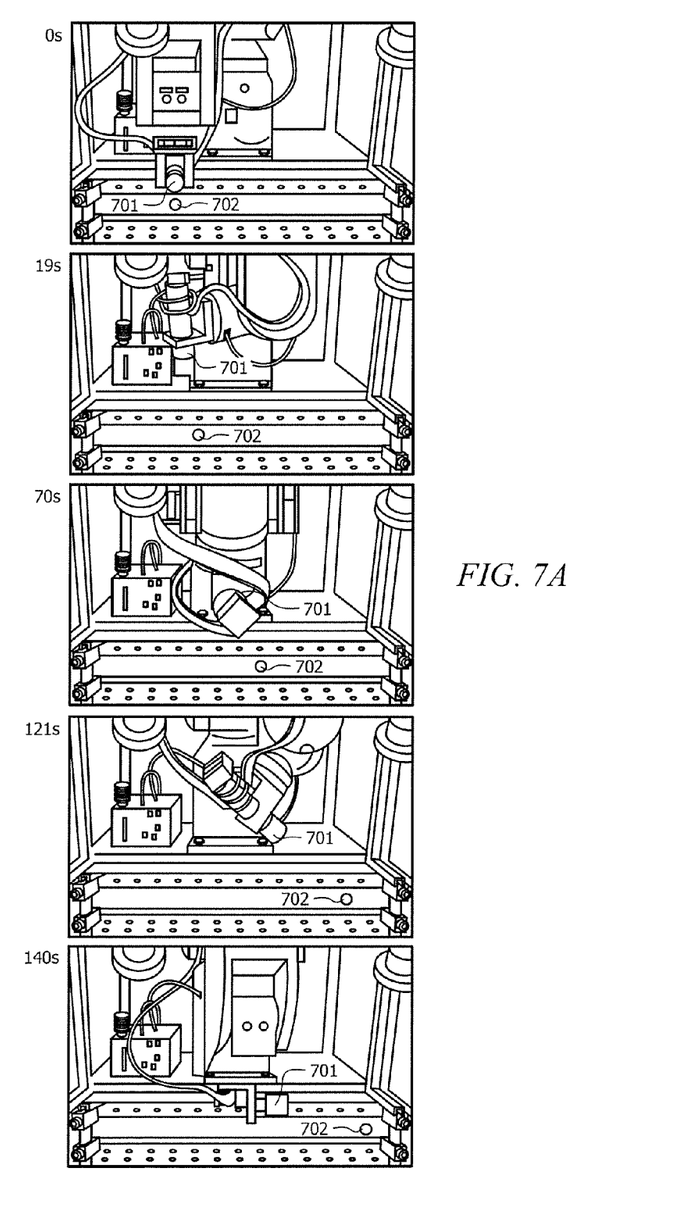
FIG. 7 illustrates the RPM actuating the spherical and threaded capsule MATs while simultaneously following a predefined, open-loop trajectory.
Figure 7B:
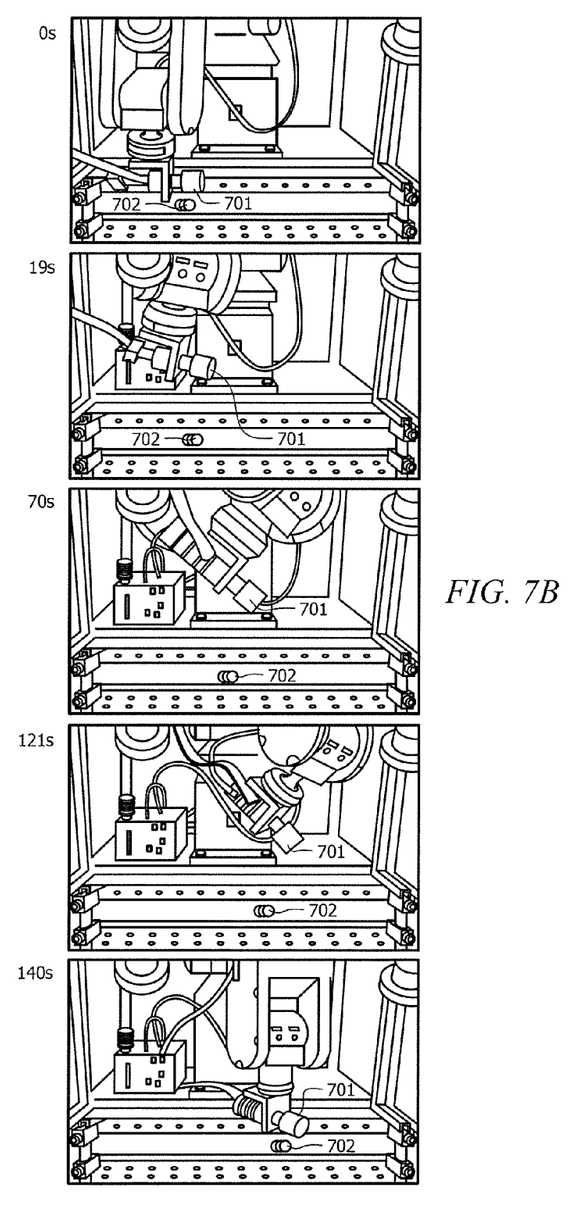
Figure 8:
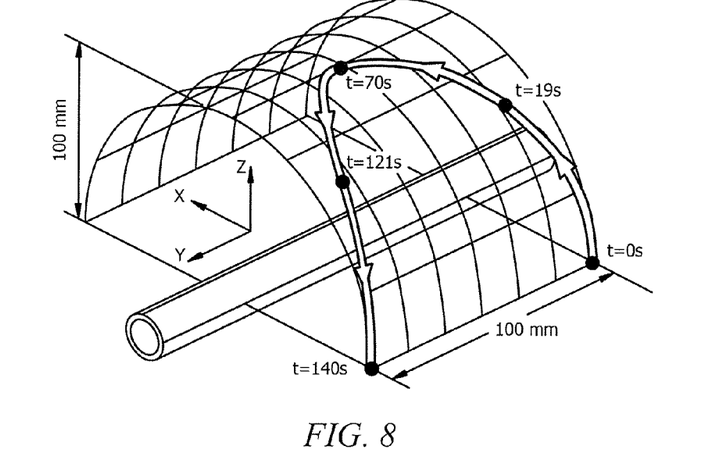
FIG. 8 shows the trajectory followed by the RPM center for experiments shown in FIG. 7.

FIG. 7 demonstrates the RPM 701 actuating the spherical and threaded capsule MATs 702 while simultaneously following a predefined, open-loop trajectory shown in FIG. 8. While the position of the RPM's 701 center follows the open-loop trajectory, the orientation of RPM 701 is adjusted according to (3) using the instantaneous MAT 702 position obtained from the vision system. Two runs along the same trajectory could, therefore, produce different RPM 701 orientation if the MAT 702 behavior varied between runs, but RPM 701 position would exactly follow the trajectory in both trials. Spherical MAT 702 is rotated with $|\Omega|=0.5$ rad/s and the threaded capsule MAT 702 is rotated with $|\Omega|=1.0$ rad/s. Each image in FIG. 7 corresponds to the equivalently labeled position in FIG. 8. In both cases, RPM 701 is rotated slowly enough so that MAT 702 is under stable, quasistatic control. Although the trajectory used herein is arbitrary, in practice, the trajectory may be planned specifically to prevent RPM 701 from colliding with a patient or other obstacle in an operating room.

All experiments shown thus far have utilized computer vision localization of a MAT through a transparent lumen. In clinical applications, the MAT may be localized using some other technique (e.g., medical imaging or magnetic localization). It is noted that these techniques may be prone to error. Because the solution for $\hat{\Omega}$ varies continuously with changing MAT position p, it is noted that while keeping $\hat{\Omega}$ fixed, there will exist a region around a nominal position p where the deviation in resulting $\hat{\omega}$ will be of sufficiently small angle that MAT propulsion is not inhibited.

Figure 9:
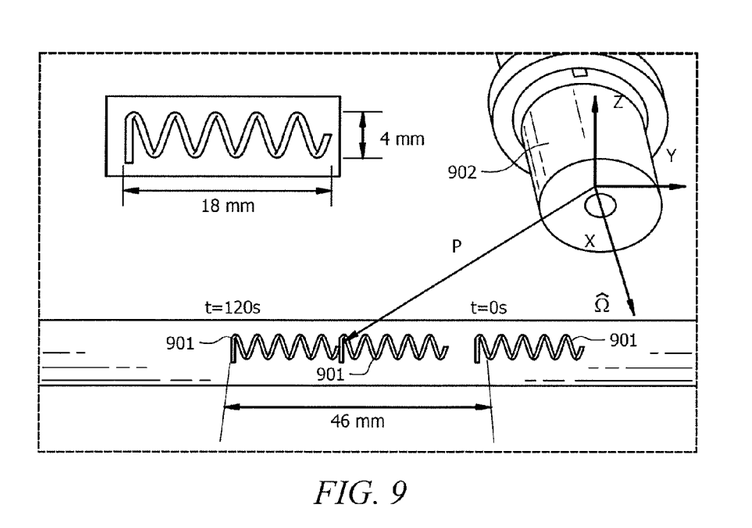
FIG. 9 shows a helical swimmer MAT, comprising a small permanent magnet rigidly attached to a helix, being propelled over a wide range of positions using an RPM with a constant position and $\hat{\Omega}$.

FIG. 9 shows a third type of MAT 901, a helical swimmer, comprising a small permanent magnet rigidly attached to a helix, being propelled over a wide range of positions using an RPM 902 with a constant position and $\hat{\Omega}$. In this example, the MAT 901 swims with an axis of rotation perpendicular to the RPM 902 axis of rotation. The image shown in FIG. 9 is a composite of four images taken 40 s apart. The position $p=[86.2,-61.0,0]^T$ mm corresponds to where $\hat{\omega}$ is parallel to the lumen. MAT 901 can swim effectively between the two extremes shown; MAT 901's position at t=0 s is the static equilibrium, at its position at t=120 s is the position at which MAT 901 steps out of synchronization with the rotating field. The inner diameter of the lumen is 5 mm. Although $\hat{\Omega}$ used in FIG. 9 produces an $\hat{\omega}$ parallel to the lumen only in the nominal position $p=[86.2,-61.0,0]^T$ mm, MAT 901 is still able to be propelled over 46 mm of the lumen. Compared to the nominal distance $|p|$, this represents a significant robustness to errors in MAT localization. As such, this example embodiment indicates that errors in MAT localization is not in itself likely to be a significant factor in the method proposed herein being clinically useful. Additionally, FIG. 9 shows propulsion of MAT 901 against the attractive force of RPM 902.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An apparatus for actuating a magnetically actuated device, the apparatus comprising:
    a rotating magnetic field source configured to generate a rotating magnetic field; and
    a guiding device configured to hold the rotating magnetic field source and reposition the rotating magnetic field source to actuate the magnetically actuated device,
    wherein the rotating magnetic field source is operable to actuate the magnetically actuated device independent of a relative orientation of the rotating magnetic field source and the magnetically actuated device, and wherein rotation of the rotating magnetic field is configured to cause propulsion of the magnetically actuated device.

2. The apparatus of claim 1, wherein the position of the apparatus is not constrained to radial and axial positions.

3. The apparatus of claim 1, wherein the rotating magnetic field source is a rotating permanent magnet (RPM).

4. The apparatus of claim 1, wherein the guiding device is configured to rotate the rotating magnetic field source.

5. The apparatus of claim 1, further comprising a vision system configured to locate the magnetically actuating device and orient the guiding device and rotating magnetic field source with respect to a located magnetically actuating device.

6. The apparatus of claim 5, wherein the vision system is one of a CT scanning device, fluoroscope device, x-ray device and ultrasound device.

7. The apparatus of claim 1, further comprising a magnetically actuated device location module configured to sense the magnetically actuated device.

8. The apparatus of claim 7, wherein said sensing includes reading an RFID signal from said magnetically actuated device.

9. The apparatus of claim 7, wherein said sensing includes sensing magnetic fields of said magnetically actuated device.

10. The apparatus of claim 7, wherein said sensing includes receiving feedback from said magnetically actuated device, said feedback providing information with respect to the rotating magnetic field source.

11. The apparatus of claim 1, wherein the guiding device is a robotic manipulator.

12. The apparatus of claim 1, wherein the rotating magnetic field source is continuously rotating during operation.

13. A method for propelling a microrobot, said method comprising:
   providing a magnetic field generating source configured to generate a magnetic field;
   rotating the magnetic field generating source about an axis of rotation, thereby creating magnetic torque at a separate point in space to act on said microrobot; and
   repositioning the magnetic field generating source during said rotation,
   wherein said rotation propels the microrobot with said created magnetic torque, and
   wherein the magnetic field generating source is operable to propel the microrobot independent of a relative orientation of the magnetic field generating source and the microrobot, such that repositioning of the magnetic field generating source follows an unconstrained trajectory with respect to the microrobot.

14. The method of claim 13, wherein the magnetic field generating source is a rotating permanent magnet.

15. The method of claim 13, wherein said microrobot is driven in rolling motion pattern.

16. The method of claim 15, wherein locating is done using a technique configured to sense the magnetically actuated device.

17. The method of claim 13, wherein said microrobot is driven in a spiraling motion pattern.

18. A method for driving a magnetically actuated device, said method comprising:
   locating the magnetically actuated device within a body of a patient;
   positioning a rotating permanent magnet proximate to said patient;
   rotating said rotating permanent magnet to provide magnetic torques to propel said magnetically actuated device; and
   repositioning said rotating permanent magnet in a manner to guide said magnetically actuated device through the patient's body, wherein the rotating permanent magnet is operable to propel the magnetically actuated device independent of a relative orientation of the rotating permanent magnet and the magnetically actuated device, such that repositioning of the rotating permanent magnet follows a free trajectory with respect to the magnetically actuated device, and accounts for workspace limitations.

19. The method of claim 18, wherein locating is done using a medical imaging system.

* * * * *